(12) United States Patent
Brady et al.

(10) Patent No.: US 7,794,497 B2
(45) Date of Patent: Sep. 14, 2010

(54) OPHTHALMIC SIZING DEVICES AND METHODS

(75) Inventors: Daniel G. Brady, San Juan Capistrano, CA (US); Tuyet H. Nguyen, Orange, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 1203 days.

(21) Appl. No.: 11/234,597

(22) Filed: Sep. 23, 2005

(65) Prior Publication Data

US 2006/0020268 A1    Jan. 26, 2006

Related U.S. Application Data

(63) Continuation-in-part of application No. 10/394,906, filed on Mar. 21, 2003, now Pat. No. 7,303,582.

(51) Int. Cl.
*A61F 2/16* (2006.01)

(52) U.S. Cl. ................................ 623/6.12; 623/912

(58) Field of Classification Search .......... 623/912, 623/6.12–6.43
See application file for complete search history.

(56) References Cited

U.S. PATENT DOCUMENTS

| | | |
|---|---|---|
| 4,077,071 A | 3/1978 | Freeman |
| 4,093,361 A | 6/1978 | Erickson et al. |
| 4,134,160 A | 1/1979 | Bayers |
| 4,174,543 A | 11/1979 | Kelman |
| 4,249,272 A | 2/1981 | Poler |
| 4,254,509 A | 3/1981 | Tennant |
| 4,254,510 A | 3/1981 | Tennant |
| 4,316,293 A | 2/1982 | Bayers |
| 4,319,564 A * | 3/1982 | Karickhoff .................. 600/587 |
| 4,370,760 A | 2/1983 | Kelman |
| 4,377,873 A | 3/1983 | Reichart, Jr. |
| 4,403,353 A | 9/1983 | Tennant |

(Continued)

FOREIGN PATENT DOCUMENTS

DE    8107675    7/1981

(Continued)

OTHER PUBLICATIONS

Alio et al. *Phakic anterior chamber lenses for the correction of myopia. Ophthalmology.* vol. 106, No. 3, Mar. 1999, pp. 458-466.

(Continued)

*Primary Examiner*—Suzette J Gherbi

(57) ABSTRACT

An apparatus for sizing an intraocular lens and/or an ocular region of the eye of a subject, such as the anterior chamber, contains a sizing device and a measurement device. In one embodiment, the sizing device comprises a first leg having a first contact portion for operably engaging the ocular portion and a second leg having a second contact portion for operably engaging the ocular portion. The sizing device has a test geometry when placed within the ocular portion. The measurement device is adapted for determining a dimension of the sizing device based at least in part on the test geometry. The sizing device may also have a reference geometry when the sizing device in a reference condition. In certain embodiments, the difference between the reference geometry and the test geometry may be used for sizing the intraocular lens and/or the ocular portion.

7 Claims, 7 Drawing Sheets

U.S. PATENT DOCUMENTS

| | | | |
|---|---|---|---|
| 4,404,694 A | 9/1983 | Kelman | |
| 4,424,597 A | 1/1984 | Schiegel | |
| 4,446,581 A | 5/1984 | Blake | |
| 4,480,340 A | 11/1984 | Shepard | |
| 4,551,864 A | 11/1985 | Akhavi | |
| 4,556,998 A | 12/1985 | Siepser | |
| 4,560,383 A | 12/1985 | Leiske | |
| 4,575,374 A | 3/1986 | Anis | |
| 4,605,409 A | 8/1986 | Kelman | |
| 4,605,411 A | 8/1986 | Fedorov et al. | |
| 4,629,460 A | 12/1986 | Dyer | |
| 4,629,462 A | 12/1986 | Feaster | |
| 4,676,791 A | 6/1987 | LeMaster et al. | |
| 4,676,792 A | 6/1987 | Praeger | |
| 4,681,102 A | 7/1987 | Bartell | |
| 4,687,484 A | 8/1987 | Kaplan | |
| 4,687,485 A | 8/1987 | Lim et al. | |
| RE32,525 E * | 10/1987 | Pannu | 623/6.48 |
| 4,725,277 A | 2/1988 | Bissonette | |
| 4,734,095 A | 3/1988 | Siepser | |
| 4,781,717 A | 11/1988 | Grendahl | |
| 4,787,904 A | 11/1988 | Severin et al. | |
| 4,834,748 A | 5/1989 | McDonald | |
| 4,834,750 A | 5/1989 | Gupta | |
| 4,863,539 A | 9/1989 | Lee et al. | |
| 4,997,442 A | 3/1991 | Barrett | |
| 5,019,097 A | 5/1991 | Knight et al. | |
| 5,047,052 A | 9/1991 | Dubroff | |
| 5,071,432 A | 12/1991 | Baikoff | |
| 5,078,742 A | 1/1992 | Dahan | |
| 5,133,749 A | 7/1992 | Nordan | |
| 5,147,395 A | 9/1992 | Willis | |
| 5,147,397 A | 9/1992 | Christ et al. | |
| 5,197,981 A | 3/1993 | Southard | |
| 5,201,763 A | 4/1993 | Brady et al. | |
| 5,203,790 A | 4/1993 | McDonald | |
| 5,217,491 A | 6/1993 | Vanderbilt | |
| 5,225,858 A | 7/1993 | Portney | |
| 5,258,025 A | 11/1993 | Fedorov et al. | |
| 5,433,745 A | 7/1995 | Graham et al. | |
| 5,476,513 A | 12/1995 | Brady et al. | |
| 5,628,796 A | 5/1997 | Suzuki | |
| 5,691,800 A * | 11/1997 | Iki et al. | 351/212 |
| 5,716,403 A | 2/1998 | Tran et al. | |
| 5,801,807 A * | 9/1998 | Satake et al. | 351/221 |
| 5,928,282 A | 7/1999 | Nigam | |
| 6,015,435 A | 1/2000 | Valunin et al. | |
| 6,051,024 A | 4/2000 | Cumming | |
| 6,129,759 A | 10/2000 | Chambers | |
| 6,179,870 B1 | 1/2001 | Sourdille et al. | |
| 6,190,410 B1 | 2/2001 | Lamielle et al. | |
| 6,200,344 B1 | 3/2001 | Lamielle et al. | |
| 6,224,628 B1 | 5/2001 | Callahan et al. | |
| 6,228,115 B1 | 5/2001 | Hoffmann et al. | |
| 6,235,055 B1 | 5/2001 | Chu | |
| 6,238,433 B1 | 5/2001 | Portney | |
| 6,261,321 B1 | 7/2001 | Kellan | |
| 6,409,763 B1 | 6/2002 | Brady | |
| 6,419,697 B1 | 7/2002 | Kelman | |
| 6,475,240 B1 | 11/2002 | Paul | |
| 6,478,821 B1 | 11/2002 | Laguette et al. | |
| 6,482,229 B1 | 11/2002 | Gwon et al. | |
| 6,598,606 B2 | 7/2003 | Henricus et al. | |
| 6,616,693 B1 | 9/2003 | Nguyen | |
| 6,723,124 B2 | 4/2004 | Brady | |
| 7,455,407 B2 * | 11/2008 | Neal et al. | 351/221 |
| 7,616,330 B2 * | 11/2009 | Neal et al. | 356/625 |
| 2001/0051825 A1 * | 12/2001 | Peterson | 623/6.12 |
| 2002/0173846 A1 | 11/2002 | Blake et al. | |
| 2003/0045933 A1 | 3/2003 | Brady | |
| 2004/0054358 A1 * | 3/2004 | Cox et al. | 606/5 |
| 2004/0068317 A1 | 4/2004 | Knight | |
| 2004/0167622 A1 * | 8/2004 | Sunalp et al. | 623/6.12 |
| 2004/0249456 A1 | 12/2004 | Cumming | |
| 2005/0251254 A1 | 11/2005 | Brady et al. | |
| 2007/0268453 A1 * | 11/2007 | Hong et al. | 351/177 |
| 2008/0018910 A1 * | 1/2008 | Neal et al. | 356/601 |
| 2008/0231809 A1 * | 9/2008 | Haigis | 351/246 |
| 2008/0269642 A1 | 10/2008 | Deacon et al. | |

FOREIGN PATENT DOCUMENTS

| | | |
|---|---|---|
| EP | 0957331 | 11/1999 |
| FR | 2745711 | 9/1997 |
| WO | 98/56315 | 12/1998 |
| WO | WO 01/54569 A1 | 8/2001 |

OTHER PUBLICATIONS

Apple et al. *Anterior chamber lenses. Part 1: complications and pathology and a review of designs.* J. Cataract Refractive Surgery. vol. 13, Mar. 1987, pp. 157-174.

Apple et al. *Intraocular lenses-evolution, designs, complications, and pathology.* Williams & Wilkins Copyright® 1989. pp. 22-36 and pp. 205-221.

Baikoff et al. *Angle fixated anterior chamber phakic intraocular lens for myopia of -7 to -19 diopters.* J. Cataract Refractive Surgery. vol. 14, May/Jun. 1998, pp. 282-293.

Marinho, A. *Results are encouraging for phakic IOLs, but more work is needed. Ocular Surgery News, Refractive Surgery.* Feb. 15, 2000, pp. 12-15.

Cilco Advertisement Brochure, Oct. 1982, 3 pages.

Praeger, Copeland Lens. 1982, 7 pages.

Strenn et al. "Capsular bag shrinkage after implantation of an open-loop silicone lens and a poly(methyl methacrylate) capsule tension ring," J Cataract Refract Surg. 1997, pp. 1543-1547, vol. 23.

Vass et al. "Prediction of pseudophakic capsular bag diameter based on biometric variables." J Cataract Refract Surg, Oct. 1999, pp. 1376-1381, vol. 25.

Tehrani et al. "Capsule measuring ring to predict capsular bag diameter and follow its course after foldable intraocular lens implantation," J Cataract Refract Surg, Nov. 2003, pp. 2127-2134, vol. 29.

U.S. Appl. No. 11/739,392, filed Apr. 24, 2007.

U.S. Appl. No. 12/412,338, filed Mar. 26, 2009.

PCT International Search Report for U.S. Appl. No. PCT/US04/08377, Mailed on Aug. 16, 2004, 3 pages.

* cited by examiner

OPHTHALMIC SIZING DEVICES AND METHODS

RELATED APPLICATION

This application is a continuation-in-part of U.S. application Ser. No. 10/394,906, filed Mar. 21, 2003 now U.S. Pat. No. 7,303,582.

BACKGROUND OF THE INVENTION

1. Field of the Invention

This invention relates generally to devices and methods for sizing a region of an eye or for sizing an intraocular lens placed inside an eye and, more specifically, to sizing devices and methods based, at least in part, on a test geometry of the sizing device after placement within the eye.

2. Description of the Related Art

The human eye is susceptible to numerous disorders and diseases, a number of which attack the crystalline lens. For example, cataracts mar vision through cloudy or opaque discoloration of the lens of the eye, and can result in partial or complete blindness. When this happens, the crystalline lens can be removed and replaced with an intraocular lens, or IOL. In certain other circumstances, an IOL can be placed in an eye containing the natural crystalline lens, for example, to provide for enhanced vision in the phakic eye.

A typical IOL comprises an optic body, or lens, adapted to focus light toward the retina of the eye, and one or more fixation members, or haptics, adapted to at least assist in supporting or fixating the IOL in a suitable location in the eye, such as the anterior chamber, ins, or capsular bag of the eye. The design of the fixation members is to a large part dictated by the location in the eye in which the IOL is to be implanted. In general, conditions in the anterior chamber are more exacting than in the posterior chamber, since the ocular structures in and around the anterior chamber are subject to distortion, for instance, when a patient squints, rubs, or touches his or her eyelids, engages in rigorous physical activity, or receives an unexpected jolt or impact to the body, particularly the face. As a result, it is desirable that anterior chamber IOLs be provided with relatively flexible fixation members that yield readily when ocular distortion occurs, in order to minimize irritation or trauma to the eye. At the same time, the fixation members must not yield so readily as to result in decentration of the IOL and distortion of the visual image. In addition, the fixation members preferably provide sufficient axial stability to prevent the optic from vaulting forwardly (and potentially contacting the cornea) in response to compressive forces on the outer edges of the IOL.

Sizing issue may arise when IOLs are placed inside the eye, for instance in the capsular bag, the sulcus, or the anterior chamber of the eye. For example, when an IOL is placed in the anterior chamber, the intraocular lens may be secured within the eye by fixating the distal ends of the anterior chamber IOL against the iridocorneal angle of the anterior chamber. It is important in this case to provide the proper fit between the IOL and the anterior chamber. Since the precise size of the anterior chamber is not easily determined prior to placement of an anterior chamber IOL, it may not be possible to determine how well an IOL will fit in the anterior chamber at the time it is implanted. If the anterior chamber IOL is too large (e.g., the separation between the distal ends of the unstressed haptics prior to placement in the eye are much larger than the diameter of the anterior chamber), this can lead to post-surgical complications such as endothelial cell loss, pupil ovulation, and/or pupillary block. Conversely, if the anterior chamber IOL is too small (e.g., the distal ends of the haptics do not extend far enough to engage the iridocorneal angle), the anterior chamber IOL may rotate, which can lead to endothelial cell loss, corneal decompensation, and/or other complications. Evidence of improper sizing of the anterior chamber IOLs may not occur until several weeks to as much as two years after the IOL has been implanted into the eye of a subject.

Accordingly, it would be advantageous to provide devices and methods for sizing an IOL and/or the region of the eye into which the IOL is to be placed at the time the IOL is implanted into the eye in order to reduce or avoid the aforementioned problems.

SUMMARY OF THE INVENTION

One aspect of the present invention involves an apparatus for sizing an intraocular lens and/or a region of the eye of a subject, such as the anterior chamber, sulcus, or the capsular bag. In one embodiment, the apparatus comprises (1) a sizing device for placement within the eye of a subject and (2) a measurement device. In such embodiments, the sizing device comprises a first leg having a first contact portion for operably engaging a first portion of the eye and a second leg having a second contact portion for operably engaging a second portion of the eye. In certain embodiments, the first and second contact portions are configured for operably engaging the iridocorneal angle of the eye. The sizing device is further comprises a test geometry when the sizing device is placed inside the eye. The measurement device is used for making a comparison between the test geometry and a reference pattern.

In one aspect of the invention, the measurement device comprises a digital camera and a microprocessor. Alternatively, the measurement device may comprise a pair of calipers or other suitable means for measuring at least a portion of the sizing device. In certain embodiments, the measurement device is a chart comprising a plurality of visual representations of the sizing device. In some embodiments, the reference pattern is a reference geometry of the sizing device in a reference condition. In other embodiments, the reference pattern is at least one visual representation of the sizing device. In still other embodiments, reference pattern is a distance between the arms of a pair of calipers. In yet other embodiments, reference pattern is empirical information regarding dimensions of the sizing device and/or empirical information correlating a geometric condition of the sizing device and a size of the sizing device.

Another aspect of the invention involves a method of sizing a region of the eye such as the anterior chamber of an eye. The method comprises supplying a sizing device according to an embodiment of the invention. The method further comprises placing the sizing device into a region of the eye such that the first and second contact portions operably engage portions of the eye such as the iridocorneal angle of the anterior chamber. The method also comprises determining the test geometry. The method further comprises determining a test geometry of the sizing device when disposed within the eye. The method additionally comprises making a comparison between the test geometry and a reference pattern. The method also comprises determining a dimension of the region of the eye based at least in part on the comparison, for example the diameter of the anterior chamber of the eye.

Yet another aspect of the present invention involves a method of sizing an intraocular lens for placement within the anterior chamber of the eye. The method comprises supplying a sizing device according to an embodiment of the invention.

The method further comprises placing the sizing device into the anterior chamber such that the contact portions of the sizing device operably engage the iridocorneal angle. The method also comprises determining the test geometry when the sizing device is disposed within the eye. The method further comprises making a comparison between the test geometry and a reference pattern. The method additionally comprises sizing an intraocular lens based at least in part on the comparison.

Still another aspect of the present invention involves a method implanting an intraocular lens into the anterior chamber of an eye. The method comprises supplying a sizing device according to an embodiment of the invention. The method further comprises placing the sizing device into the anterior chamber such that the contact portions of the sizing device operably engage the iridocorneal angle. The method also comprises determining the test geometry when disposed within the eye. The method further comprises making a comparison between the test geometry and a reference pattern. The method additionally comprises determining a dimension of at least one of the sizing device and the anterior chamber based at least in part on the comparison. The method also comprises placing an intraocular lens into the anterior chamber. The method may further comprise reconfiguring the sizing device is reconfigured to form an intraocular lens.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following 12 figures, with like numerals indicating like parts.

DETAILED DESCRIPTION OF THE DRAWINGS

Figure 1:
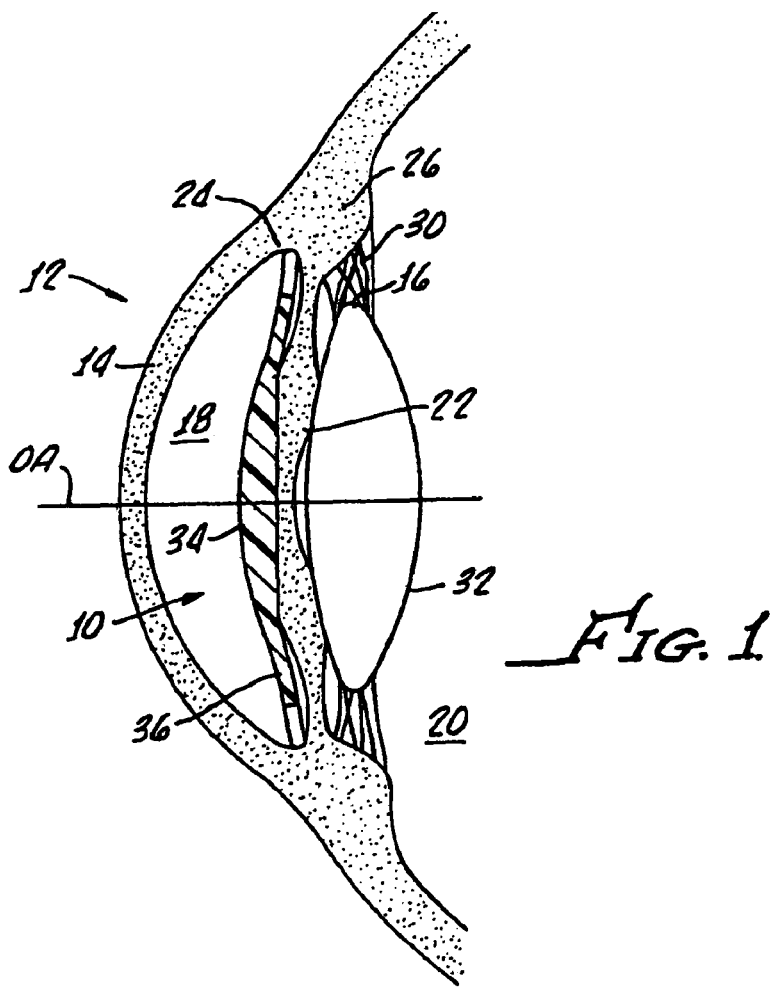
FIG. 1 is a cross-sectional view through a sagittal portion of a human eye illustrating a sizing device according to an embodiment of the present invention mounted in the anterior chamber.
Figure 2:
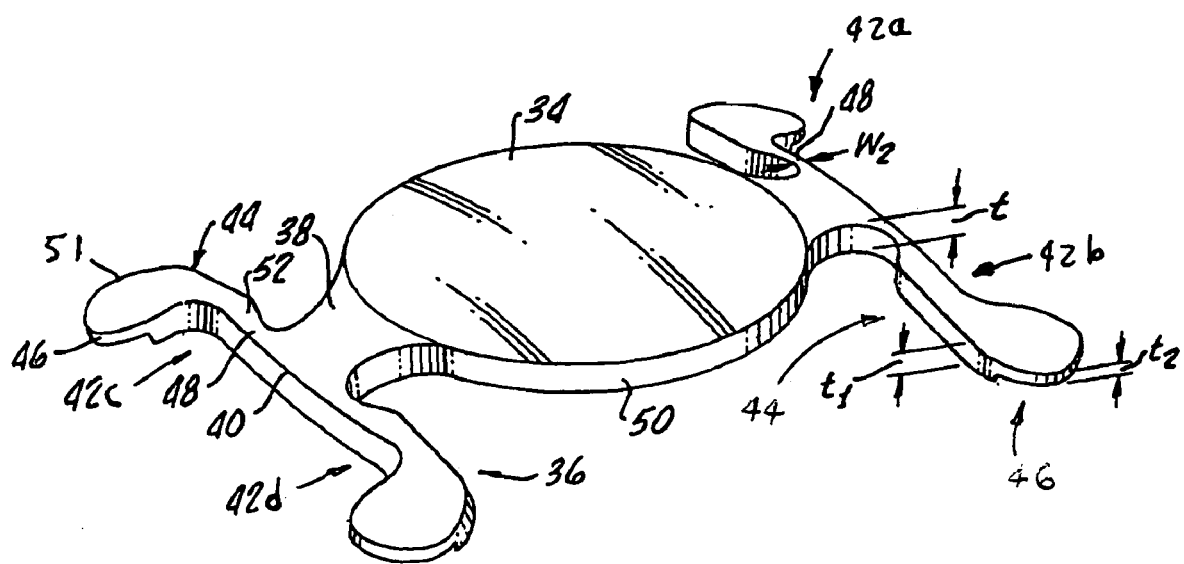
FIG. 2 is a perspective view of the sizing device illustrated in FIG. 1.

The present invention generally relates to sizing devices and methods of use thereof related to the implantation and use of intraocular lenses (IOLs). For example the sizing device may be used for sizing an IOL, sizing a region of an eye into which an IOL is to be placed, and/or determining the force produced by an IOL on the eye. Sizing devices according to embodiments of the invention offer certain advantages over currently available IOLs and/or methods of insertion into the eye of a subject. For example, the sizing device may be used to determine if the IOL is improperly sized at the time of implantation, rather than weeks or even years after the IOL has been implanted and damaged the eye. In the event an IOL according to embodiments of the invention is not correctly sized when initially inserted, corrective measures may be taken during the initial surgery to immediately correct the situation and prevent future damage to the eye. The IOL may advantageously be explanted during the initial surgery without the need for a new incision in the eye. Once explanted, the IOL may be replaced by a different IOL that provides a predetermined fit within the subject's eye.

The sizing device may be an ophthalmic device specifically configured only for the task of sizing a region of the eye into which an IOL is to be place (e.g., the anterior chamber or sulcus, and/or to size an IOL). In such embodiments, the sizing device is preferably configured to allow selection of an IOL that will provide a predetermined fit between IOL and the region of the eye into which the IOL is to be placed, thereby advantageously reducing the possibility of post-surgical problems such as endothelial cell loss, pupil ovulation, pupillary block, rotation of the IOL, corneal decompensation, etc. Once the IOL is selected, the sizing device may be removed and a properly sized IOL providing a predetermined fit may be inserted into the eye.

Alternatively, the sizing device may be the IOL itself and remain in the eye after completion of the sizing task. In such embodiment, the sizing device is preferably configured to provide a predetermined fit between IOL and the region of the eye into which the IOL is to be placed. If the sizing device is determined not to provide the predetermined fit, then the sizing device may be explanted and replaced by an IOL and/or another sizing device that provides a predetermined fit.

In another alternative, the sizing device comprises a separate optic that is not initially implanted with the sizing device. In such cases, the optic may be attached to the sizing device to form an IOL, once it is determined that the sizing device provides a predetermined fit inside the eye. In the event that the sizing device does not provide the desired predetermined fit within the eye, the sizing device may be explanted and replaced by an IOL and/or another sizing device that provides the desired fit.

As used herein, the terms "to size" or "sizing" mean to determine, using either direct or indirect means, at least one dimension of an object, for instance an IOL or a region of an eye into which the IOL has been or will be placed. The term "to size" or "sizing", when applied to an IOL, may also mean to select an IOL from a plurality of candidate IOLs in order to provide a predetermined fit between the IOL and the region of the eye into which the IOL is placed or will be placed.

As used herein, the term "fit", means the degree of closeness or degree of contact between the surfaces of mating portions of a plurality of objects, for instance between a sizing device (and/or an IOL) and the region of the eye into which the sizing device (and/or IOL) is placed. As used herein, the term "fit" also include cases where there is no contact or only partial contact between the sizing device and/or IOL and the region of the eye.

As used herein, the term "determine" includes, but is not limited to (1) measuring a coordinate, distance, angle, area, volume, or other characteristic of an individual feature or between two or more features of an object (e.g., measuring the distance between a first feature and a second feature of a sizing device before and/or after placement inside an eye), (2) estimating, either quantitatively or qualitatively, a dimension, angle, or shape or of an object or portion thereof for comparison to a reference pattern, and (3) calculating a coordinate, distance, angle, area, volume, or other measurable characteristic of an individual feature or between two or more features of an object based on one or more measurements (e.g., calculating the diameter of the anterior chamber of the eye by subtracting a reference distance between two features of a sizing device when in a reference condition from a test distance between those same two features when the sizing device placed within the anterior chamber). The meaning of the term "determine" also includes measuring, estimating, or calculating physical characteristics of or associated with an object such as force, torque, temperature, mass, optical transmittance, refractive index, etc. The determination may be either direct or indirect. An example of an indirect determination includes, but is not limited to, making a digitized image of a sizing device inside the anterior chamber of an eye and using the digitized image to indirectly determine the size of the sizing device and, therefore, the size or dimension of the anterior chamber. This may done by establishing a scale relationship between pixel space in the image and actual distances between features of the sizing device. In another example, a determination may involve a visual comparison between of an object, for example comparison of a sizing device, with a chart or reticle containing a plurality or series of photographs, templates, or other visual representations of the sizing device.

Referring now to FIG. 1, a sizing device according to a first embodiment of the present invention comprises an IOL 10 that is implanted in an eye 12. The eye 12 comprises a cornea 14 shown to the left or front of the eye and an annular iris 16 shown in the middle of the eye. The iris 16 divides the eye 12 into an anterior chamber 18 at the front of the eye and a posterior chamber 20 in back of the iris. The iris 16 also defines the aperture or pupil 22, which is a variable opening in the middle of the iris. The posterior face of the cornea 14 and the anterior face of the iris 16 meet at the scleral spur defining an iridocorneal angle 24. Behind the iris 16 is the ciliary process 26, which controls the movements of the natural crystalline lens 32 of the eye 12 via a plurality of fibrous zonules 30. The IOL 10 may be configured for sizing a region of the eye 12 such as the anterior chamber 18, for determining the size, fit, asymmetry or some other parameter of the IOL 10 after it has been placed within the eye 12, and/or for determining the force produced by an IOL on at least some portion of the eye 12.

Figure 3:
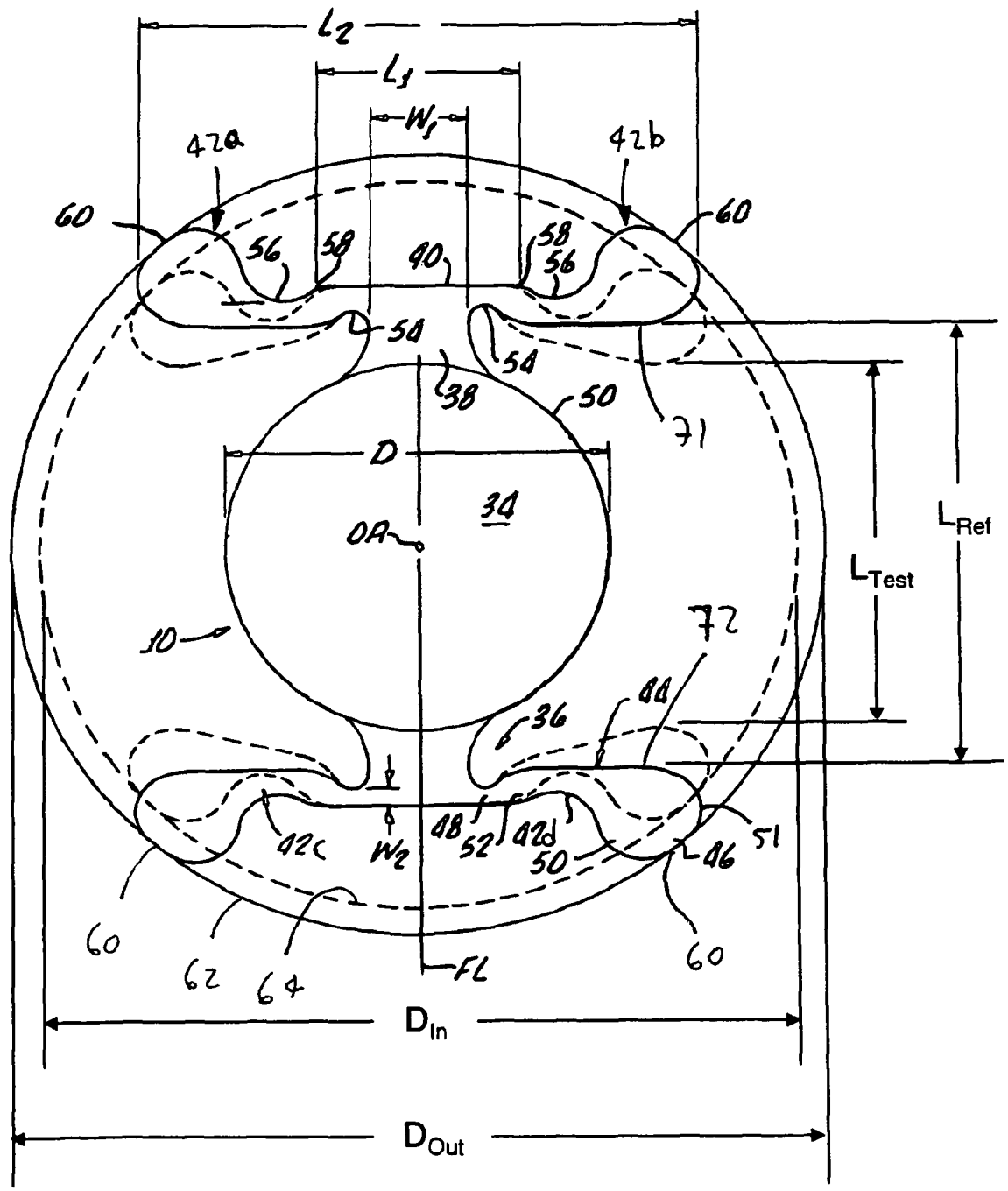
FIG. 3 is a frontal view of the sizing device shown in FIG. 1 illustrating sizing features of the sizing device.
Figure 4:
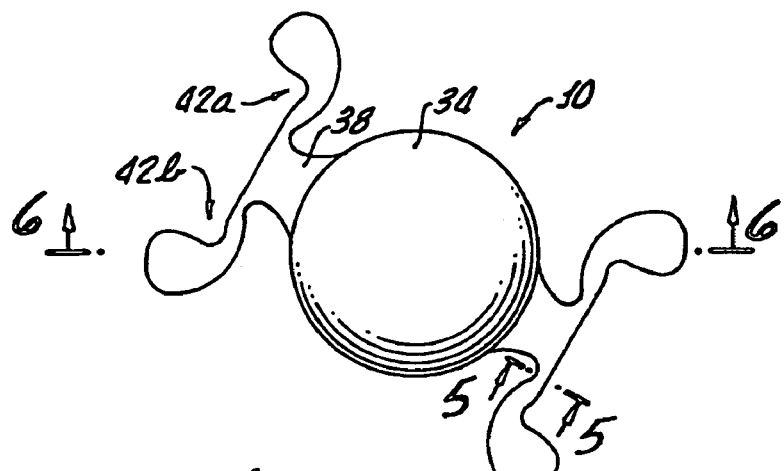
FIG. 4 is a frontal elevational view of the sizing device illustrated in FIG. 1.
Figure 5:
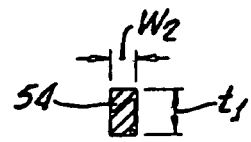
FIG. 5 is a sectional view taken through line 5-5 of FIG. 4.
Figure 6:
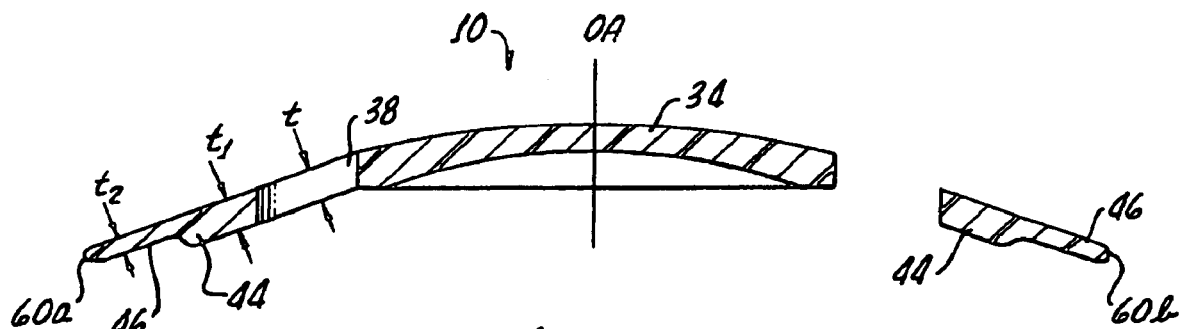
FIG. 6 is a sectional view taken through line 6-6 of FIG. 4.

Still referring to FIG. 1, with additional reference to FIGS. 2 through 6, the IOL 10 comprises an optic 34 that is supported in front of the pupil 22 by one or more fixation members 36, sometimes known as haptics. In certain embodiments, for example as illustrated in FIG. 3, the IOL 10 comprises two fixation members 36; however, in other embodiments the IOL 10 may comprise more or fewer fixation members than shown in FIG. 3. The fixation members may have different configurations than those illustrated in FIG. 3 and/or that are different from one another. The fixation members 36 in the illustrated embodiment extend radially outwardly from the typically circular optic 34 to rest in and against or in contact with the iridocorneal angle 24 and, as will be explained below, may be designed to reduce retention forces and inhibit forward vaulting of the optic along the optical axis OA. The optical axis OA is an imaginary line that passes through the optical centers of both the anterior and posterior surfaces of the IOL 10, and in the human eye is generally aligned along the centers of the cornea 14, the natural lens 32 and the retina (not shown) of the eye 12. Desirably, the optical axis OA of the IOL 10 coincides with that of the natural eye.

When used as a refractive lens, the optic portion 34 of the IOL 10 can be a positive powered lens from 0 to approximately +20 or more Diopters, or a negative powered lens from 0 to approximately −25 or less Diopters. The optic portion 34 can be biconvex, plano-convex, plano-concave, biconcave or concave-convex (meniscus), depending, for instance, upon the needs of the patient. In addition, the optic portion 34 may have a single optical power or may be multi-focal. The optic portion 34 may employ, for example, refractive or diffractive effects to provide either a monofocal or multi-focal lens. In certain embodiments, the optic portion 34 may include aspheric and/or diffractive portions on at least one surface, for example to reduce or substantially eliminate one or more optical aberrations of the IOL 10 and/or the eye 12, for example spherical and/or chromatic aberrations.

The IOL 10 can be made from a variety of so-called soft biocompatible materials that can be folded, deformed, or compressed, such as silicone polymeric materials, acrylic polymeric materials, hydrogels, hydrogel-forming polymeric materials and mixtures thereof. The fixation members 36 may be formed separately from the optic portion 34 and connected through processes such as heat and/or physical staking and/or chemical bonding, or may be formed integrally with the optic portion 34 in a so-called single-piece IOL. In a preferred embodiment, the IOL 10 is made of a material, such as a cross-linked acrylic polymeric material, that can be folded for insertion through a small incision (e.g., less than 3.5 mm), and is desirably of a unitary, one-piece construction. At least portions of the IOL 10 may be made of a more rigid material, including such polymeric materials as polypropylene, polymethylmethacrylate PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitinol, and the like.

The optic 34 of the IOL 10, which is typically circular and symmetrical about a fold line FL, has a diameter D that is preferably in the range of about 5.5 to about 6.5 mm, depending on the size of the patient's eye, and a peripheral edge 50, the thickness of which depends on the patient's prescription and other factors.

Each fixation member 36 may include an intermediate portion, or plate, 38 that extends from a peripheral edge 50 of the optic 34 to a straight outer edge 40. Alternatively, one of the fixation members 36 may be configured with an intermediate portion 38, while the other fixation members 36 have a different configuration. Preferably, pairs of legs 42a, b and 42c, d intersect the intermediate portions 38 at the outer edges 40. The legs 42a, b and 42c, d preferably extend in opposite directions to one another, generally perpendicular to the fold line FL.

In the illustrated embodiment, the intermediate portion 38 of each fixation member 36 has a uniform, or substantially uniform, axial thickness t that is equal to or less than, but not substantially less than, the peripheral edge 50 of the optic 34. In addition, the intermediate portion 38 preferably has a width $w_1$ measured in a generally tangential direction (perpendicular to the fold line FL). This width $w_1$ may be substantially constant between the peripheral edge 50 of the optic 34 and the straight outer edge 40 of the intermediate portion 38, although it may decrease slightly in the distal direction. In addition, in certain embodiments, the width $w_1$ is preferably greater than the axial thickness t throughout the length of the intermediate portion 38.

Each of the legs 42a-d may further include a proximal portion 44 having a first, uniform or substantially uniform, axial thickness $t_1$, and a terminal portion 46 having a second, uniform or substantially uniform, axial thickness $t_2$. The thickness $t_1$ of the proximal portion 44 may advantageously be equal to or less than, but preferably not substantially less than, the thickness t of the intermediate portion 38, and greater than the thickness $t_2$ of the terminal portion 46.

The proximal portion 44 of each leg 42-d may include a reduced width region 48 near the intermediate portion 38, and an enlarged pod region 51 near the terminal portion 46. In the illustrated embodiment, the reduced width region 48 is joined to the pod region 51 by an elongated bridge region 52. The reduced width region 48 advantageously has a width $w_2$, measured in a generally radial direction (parallel to the fold line FL), that is less than the axial thickness $t_1$, at that point. The reduced width region 48 of each leg 42a-d acts essentially as a hinge or pivot point allowing that leg 42a-d to flex about the intermediate portion 38 in response to compressive forces, while the intermediate portion 38 and optic 34 remain substantially stationary.

In the illustrated embodiment, each leg 42a-d of each fixation member 36 includes an inner edge 54 that curves inwardly at its intersection with intermediate portion 38 to form the reduced width region 48, and an outer-edge 56 that merges at a proximal end 58 with the straight outer edge 40 of the intermediate region 38. The proximal ends 58 of adjacent legs 42a-d are separated from one another by the length $L_1$ of the straight outer edge 40, which advantageously is at least about 1.5 mm long.

The terminal portion 46 of each leg 42a-d is preferably curved and includes a contact portion 60 that substantially matches the contour of the iridocorneal angle 24 of the eye 12 so that it can be comfortably received therein. Each pair of legs 42a, b and 42c, d are spaced apart from one another at distalmost points by a distance $L_2$ that is longer than the diameter D of the optic 34.

The solid lines of the IOL 10 in FIG. 3 show the IOL 10 as it might appear in a relaxed, uncompressed state. If the IOL 10 were place in the anterior chamber 18 in this uncompressed state, it would tend to slide or otherwise move from its central position. The dashed lines of the IOL 10 show the IOL 10 in a compressed configuration that would result as the walls of the chamber 18 produce compressive forces against each of the terminal regions or pods 44, causing the legs 42a, b to flex or pivot inwardly about the reduced width region 48. At the same time, the intermediate region 38 and the optic 34 would remain stable and relatively unaffected by the compression imparted by the surrounding eye. As a result, the optic 34 in the illustrated embodiment undergoes little radial compression, and remains substantially in place and centered along the optical axis OA.

The dimensions of the various elements of the IOL 10 relative to one another are preferably selected to achieve increased stability of the IOL 10 within the anterior chamber 18 of the eye 12. More specifically, the geometry and relative dimensions of the various elements may be selected such that compressive forces exerted on the legs 42a-d will cause the legs 42a-d to flex about the intermediate region 38, while the intermediate region 38 and the optic 34 will tend to remain stationary.

In certain embodiments, as illustrated in FIG. 3, the geometry and relative dimensions of the various elements reduce the potential for problems during release of the IOL 10 from an insertion apparatus. For instance, the relatively large distance $L_2$ between the terminal regions 46 of adjacent legs 42a-d reduces the possibility of the terminal regions 46 coming into contact with, and sticking to, either the optic 34 or the rod of an insertion device (not shown). In addition, the straight edge 40 of the intermediate portion 38 provides an elongated flat surface for the insertion rod to contact. The legs 42a-d of the fixation members fold along either side of the rod, but make little or no actual contact with the rod because of the spacing provided by the edge 40. Also, because the legs 42a-d extend substantially parallel to a diameter of the optic 34 and are not significantly angled in a distal or proximal direction, the fixation members 42a-d tend to deploy in a planar fashion, with a minimum anterior/posterior profile. Because of this minimum profile, the IOL 10 can be manipulated relatively safely within the limited space available in the phakic anterior chamber, with reduced risk of contacting and damaging the natural crystalline lens and/or the endothelium lining.

The IOL 10 can be effectively inserted into an anterior chamber of an eye and used to provide vision correction, for example, vision enhancement. In a typical situation, the IOL 10 may be placed in the load chamber of an IOL insertion cartridge (not shown) having folding leaves and a hollow distal tip. The leaves of the cartridge are moved from their open position to their closed position, bringing both the optic and fixation members into a folded or rolled configuration. The cartridge is then placed in a suitable insertion apparatus such that the distal tip of the cartridge projects through an distal opening in the insertion apparatus. The distal tip of the cartridge is then placed in or near a very small incision in the sclera or cornea of an eye 12, and a plunger or the like is advanced through the insertion apparatus, causing the IOL 10 to be passed through the outlet of the distal tip into the anterior chamber 18 of the eye. Once placed in the anterior chamber 18, the IOL 10 may, if necessary, be repositioned using a needle or the like to obtain optimum stability and centration.

In certain embodiments, the legs 42a-d are used to size or determine a dimension of the IOL 10 and/or the anterior chamber 18. As illustrated in FIG. 3, for instance, when the IOL 10 is outside the eye, it is characterized by a diameter $D_{out}$ corresponding to the diameter of a circle 62 substantially intersecting the contact portions 60. By contrast, when inside the eye, the IOL 10 is characterized by a diameter $D_{in}$ corresponding to the diameter of a circle 64 substantially intersecting the contact portions 60 when the IOL 10 is compressed inside the eye 12. The IOL 10 may further comprise a first feature 71 (e.g., an edge of the leg 42b) and a second feature 72 (e.g., an edge of the leg 42d). The distance between the first and second features 71, 72 is characterized by a distance $L_{Ref}$ when the IOL 10 is outside the eye and a distance $L_{Test}$ when the IOL 10 is inside the eye. In certain embodiments, a size of the IOL 10 inside the eye may be determined by measuring either the distance $L_{Test}$ or by measuring both the distance $L_{Test}$ and the distance $L_{Ref}$. In other embodiments, the size of the IOL 10 may be determined by comparing the distance between or relative orientation of the first and second features 71, 72 to a series of photographs, templates, or other visual representations of the IOL 10 under varying amounts of compression.

Figure 7:
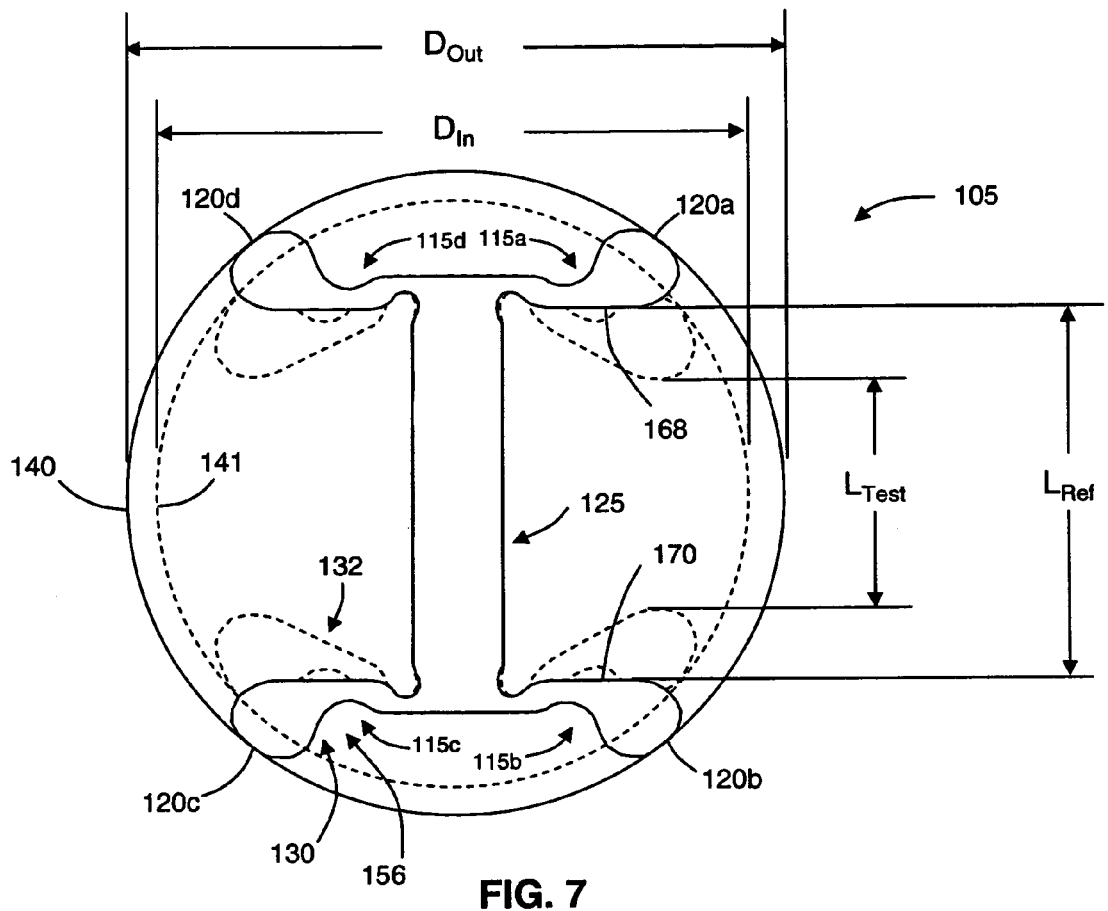
FIG. 7 is a frontal view of the sizing device according to another embodiment of the present invention.
Figure 8:
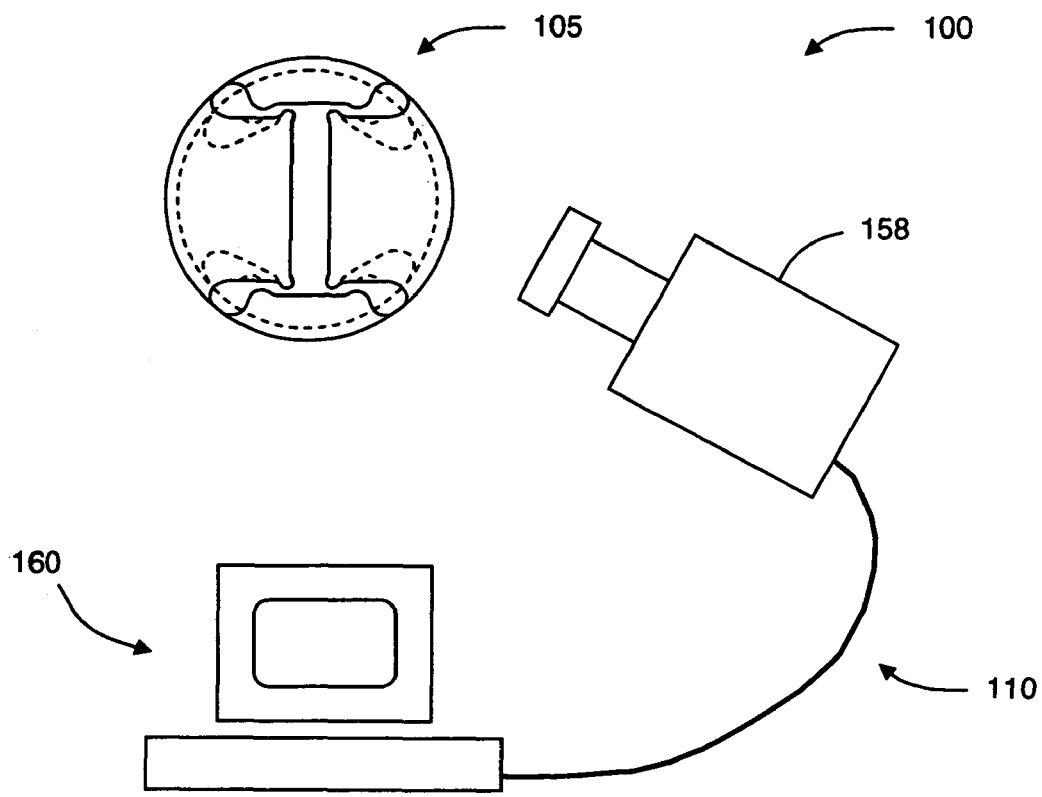
FIG. 8 is a frontal view of a sizing apparatus according to embodiments of the present invention.

Referring to FIGS. 7 and 8, in certain embodiments, an apparatus 100 for sizing an IOL or a region of an eye comprises a sizing device 105 for placement within the eye 12 and a measurement device 110. For example, the sizing device 105 in FIG. 7 may be configured for sizing the anterior chamber 18 of the eye 12 and/or for sizing an IOL to be placed within the anterior chamber 18. The sizing device 105 comprises plurality of legs 115a, b, c, and d having respective contact portions 120a, b, c, and d for operably engaging the iridocorneal angle 24.

In the illustrated embodiment, the sizing device 105 further comprises a body 125 to which the plurality of legs 115a-d are joined. The body 125 is preferably relatively rigid in comparison to the plurality of legs 115a-d, either by being relatively thick in one or more dimensions as compared to portions of the legs 115a-d and/or by being made of a material that is stiffer than the material from which the legs 115a-d are made. For example, the legs 115a-d of the sizing device may be made of a relatively soft material such as silicone, while the body 125 is made of a relatively hard material such as PMMA. Alternatively, the entire sizing device 105 may be formed of a single material, such as a silicone or acrylic material, and configured such that the body 125 is stiffer than the legs 115a-d. Preferably, the body 125 is relatively narrow (e.g., compared to the diameter of the optic 34 of the IOL 10) so that it may be easily implanted into and/or explanted from the eye 12.

The sizing device 105 is configured such that it comprises a reference geometry 130 when it is in an unstressed condition or some other referenced condition, for example, when the sizing device 105 is exposed to a predetermined amount of compressive force. This will generally be the geometry the sizing device 105 prior to placement within the eye 12. Once the sizing device 105 is placed within a region of the eye 12, for example in the anterior chamber 18, it has test geometry 132 that is preferably different than the reference geometry 130. As used herein in reference to the sizing device 105 or the IOL 10, the term "geometry" refers to the relationship of the various features (e.g., points, apexes, corners, centers, angles, edges, surfaces, solids, and shapes such as a line, arc, circle, triangle, rectangle, etc.) of the sizing device 105 or the IOL 10 and the dimensions of and/or between these features. As used herein, the term "dimension" includes, but is not limited to the length, angle, area, perimeter, diameter, or volume of and between features of a device or apparatus such as the sizing device 105 or the IOL 10.

In the illustrated embodiment in FIG. 7, the sizing device 105 is contained within a circle 140 when configured to have the reference geometry 130 and within a circle 141 when configured to have the test geometry 132. The circles 140, 141 are preferably defined as circles passing through the contact portions 120a-d when the sizing device 105 has either the reference geometry 130 or the test geometry 132.

As illustrated in FIGS. 7 and 8, the sizing device 105 may be configured for sizing or determining a dimension of the sizing device 105 or a region of the eye 12. In such configurations, the sizing device 105 is preferably removed after the sizing task is completed and replaced by an IOL selected to have a dimension for providing a predetermined fit inside the eye. In other embodiments, the sizing device 105 is configured to remain in the eye. In such embodiments, the sizing device 105 may be an IOL, such as the IOL 10.

Figure 9:
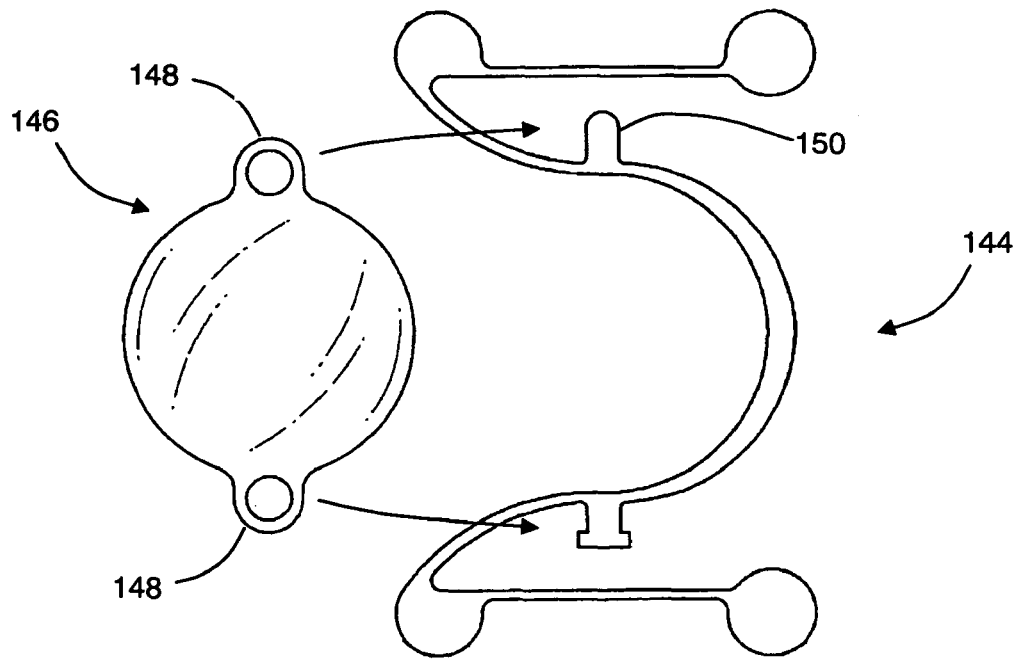
FIG. 9 is an alternative embodiment of a sizing device comprising a frame and an attachable optic.

Referring to FIG. 9, in certain embodiments the sizing device 105 may comprise a frame 144 and an attachable optic 146: In such embodiment, the frame 144 is configured for placement within the eye 12 for the purpose of performing a sizing task such as, for example, sizing a region of the eye 12 such as the anterior chamber 18, determining the size, fit, asymmetry, or some other parameter of the frame 144 after it has been placed within the eye 12, and/or determining the force produced by the frame 144 on at least some portion of the eye 12. Once the sizing task is completed, the attachable optic 146 may be attached to the frame 144, preferably while the frame 144 is still in the eye 12. The optic 146 may be attached to the frame 144 mechanically, for example as disclosed in U.S. Pat. No. 6,419,697 and U.S. Patent Application No. 2002/0173846, which are herein incorporated by reference. In the illustrated embodiment in FIG. 9, the attachable optic 146 comprise eyelets 148, which may be inserted into tabs 150 of the frame 144. Alternatively or additionally, the attachable optic 146 may be attached to the frame 144 using some type of biocompatible adhesive, for example a epoxy compound that is cured using heat or UV light.

The measurement device 110 is used to make a comparison between the test geometry 132 and a reference pattern 156. In certain embodiments, the reference pattern 156 comprises the reference geometry 130 of the sizing device 105; however, other reference patterns 156 may be used, as discussed in greater detail below herein.

In the illustrated embodiment in FIG. 8, the measurement device 110 comprises a camera 158, such as a digital camera, and a processor 160, as illustrated in FIG. 8. In such embodiments, the camera 158 preferably interfaces with and/or is controlled by the processor 160. The processor 160 may comprise a computer, such as a personal computer (PC) or laptop computer, a processor chip and associated supporting electronics and input/output hardware, or any other electronic device or system suitable for controlling the camera 158 and/or for receiving, processing, and/or outputting information provided by the camera 158.

In such embodiments, the reference pattern 156 may be either a digitized image of reference geometry 130 or data provided by the manufacturer or supplier regarding dimensions or relationships of certain features of the sizing device 105. In any event, the reference pattern 156 may be compared to a digitally recorded image of the test geometry 132 in order to provide the desired sizing information for the sizing device 105, an IOL to be placed in the eye 12, and/or the region the eye into which the sizing device 105 has been placed.

In other embodiments, the measurement device 110 may alternatively or additionally comprise a pair of calipers or some other mechanical, optical, electronic, or optoelectronic device capable of measuring one or more distances and/or angles of the sizing device 105. When the measurement device 110 is a pair of calipers, the reference pattern 156 may be a distance between two arms of the calipers obtained when the calipers are adjusted to measure a distance between features of the measurement device 105.

Figure 10:
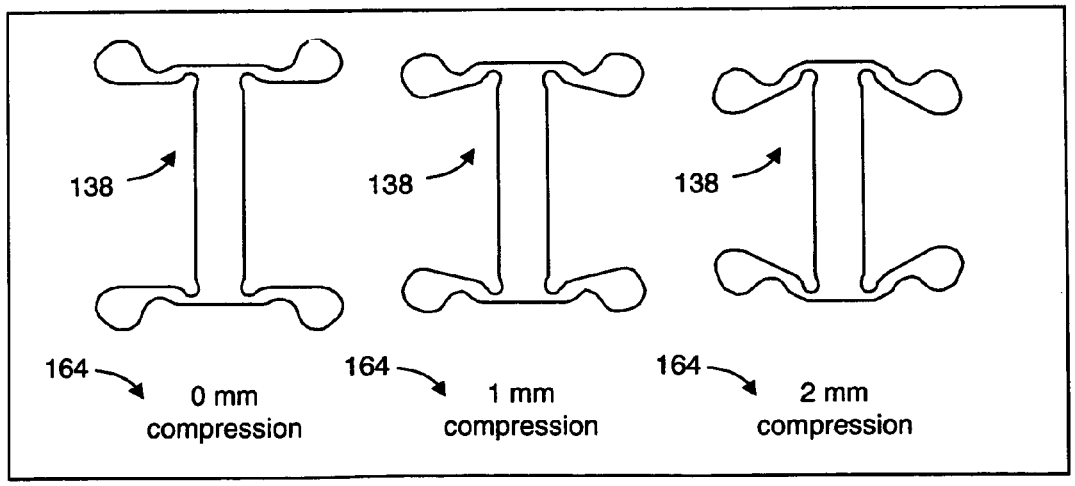
FIG. 10 is front view of a chart used in certain embodiments of the present invention.

Referring to FIG. 10, in still other embodiments, the measurement device may comprise a chart or reticle 162 containing a plurality or series of photographs, templates, or other visual representations 138 of the sizing device 105. In such embodiments, the reference pattern 156 comprises at least one of the series of visual representations 138. Thus, the chart or reticle 162 may be used for making a comparison between the visual representations 138 and the test geometry 132 of the sizing device 105 disposed in the eye 12. Preferably, the visual representations 138 in the chart or reticle 162 illustrate the geometry of a least a portion of the sizing device 105 under varying amounts of compression. For instance, in the illustrated embodiment in FIG. 10, the visual representations 138 illustrate varying amounts of bending of the legs 115a-d corresponding to varying amounts of compression of the sizing device 105. Each visual representation 138 may be generated from the sizing device 105 itself or from another device that represents or models at least a portion of the sizing device 105 under different conditions (e.g., under varying amounts of compression). Each visual representation 138 may be associated with data about the sizing device 105 under a specified condition. For example, the visual representations 138 may comprise text blocks 164 disposed proximal each visual representation 138, wherein the text blocks 164 indicate the amount of compression associated with a particular test geometry 132 of the sizing device 105.

In the illustrated embodiment, the sizing device 105 and the corresponding reference and/or test geometries 130, 132 comprise a first feature or characteristic 168 and a second feature or characteristic 170 adapted for sizing an IOL or region of eye 12. In the illustrated embodiment in FIG. 7, the first feature 168 corresponds to an edge portion of the leg 115a and the second feature 170 corresponds to an edge portion of the leg 115b. Alternatively, the sizing device 105 and the corresponding reference and/or test geometries 130, 132 may comprise only a single feature adapted for sizing an IOL or region of eye 12. The reference geometry 130 may include a reference distance $L_{Ref}$ and/or a reference angle (not illustrated) between the first and second features 168, 170 prior to placement within the eye 12. The test geometry 132 may include a test distance $L_{Test}$ and/or a test angle (not illustrated) between the first and second features 168, 170. In such embodiments, the apparatus 100 is adapted to size the sizing device 105, an IOL, and/or a region of the eye, for example, by comparing the reference distance $L_{Ref}$ to the test distance $L_{Test}$ and/or the reference angle to the test angle.

Figure 11:
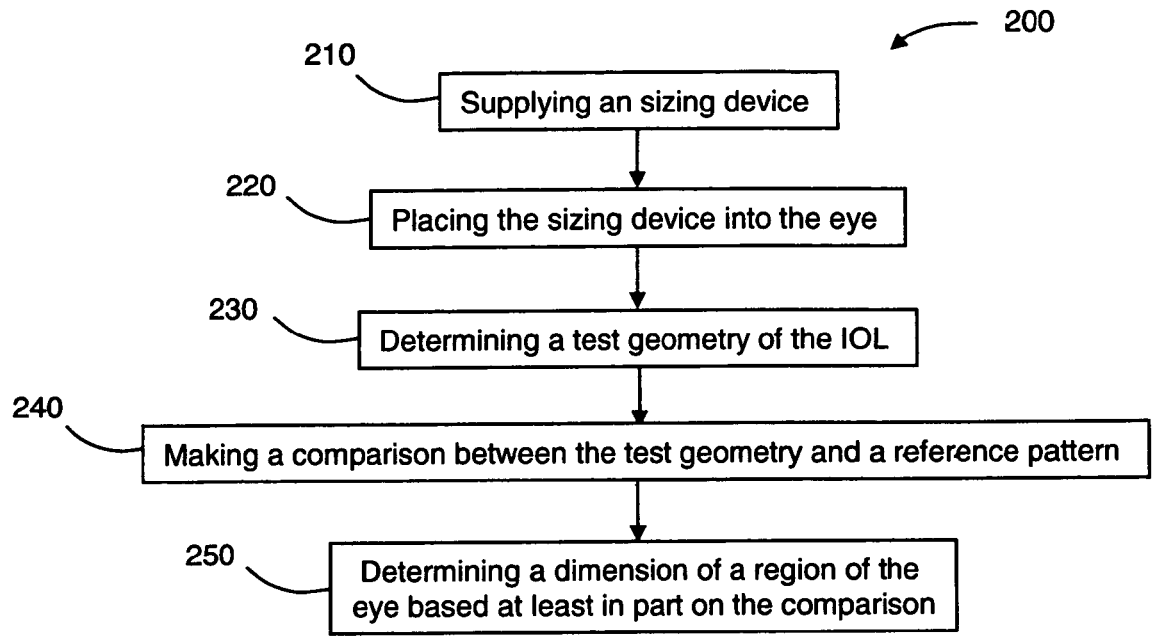
FIG. 11 is a block diagram of a method of sizing a region of an eye into which an IOL is to be placed.

Referring to FIGS. 7-8, and 11, in certain embodiments, a method 200 is illustrated for sizing a region in an eye into which the sizing device 105 is placed, for example, the anterior chamber 18 of the eye 12. The method 200 may also be used to size other regions of an eye, for example the capsular bag or sulcus. The method 200 comprises an operational block 210, which comprises supplying the sizing device 105 for placement within the region of the eye. The method 200 further comprises an operational block 220, which comprises placing the sizing device 105 into the region of the eye such that contact portions of the sizing device 105 operably engage one or more portions of the eye. For example, when the sizing device 105 may be placed within the anterior chamber 18 and the contact portions 120a-d operably engage the iridocorneal angle 24 of the eye 12. The method 200 also comprises an operational block 230, which comprises determining the test geometry 132 of the sizing device 105. The method 200 additionally comprises an operational block 240, which comprises making a comparison between the test geometry 132 and the reference pattern 156. The method 200 also comprises an operational block 250, which comprises determining a dimension of the region of the eye into which the sizing device 105 is placed based at least in part on the comparison between the test geometry 132 and the reference pattern 156.

In a non-limiting example, the method 200 is described below for embodiments in which the sizing device 105 is used to size the anterior chamber 18 of the eye 12. In such embodiments, the operational block 220 comprises placing the sizing device 105 into the anterior chamber 18. The sizing device 105 may be inserted or injected into the anterior chamber 18 using forceps, an inserter or injector device, or other devices or means suitable for the task. Once the sizing device 105 is inserted into the eye 12, it is preferably manipulated until the sizing device is suitably centered within the eye and at least some of the contact portions 120a-d operably engage the iridocorneal angle 24.

In operational block 230, the test geometry 132 of the sizing device 105 is determined. Preferably the test geometry 132 is different from the geometry of sizing device 105 prior to placement inside the anterior chamber 18 (e.g., the reference geometry 130). Determining the test geometry 132 may include measuring the test distance $L_{test}$, for example by processing a digitized image of the sizing device 105. In other embodiments, a test angle may be used instead of or in addition to the test distance $L_{test}$ as a means of determining the test geometry 132. Since the sizing device 105 is generally disposed inside the eye 12, determination of the test geometry is preferably established using indirect means, for example by making a digitized image of at least a portion of the sizing device 105. Alternatively, determining the test geometry may include more qualitative means, such as estimating a distance or angle between features of the sizing device 105, noting the relative locations and/or orientations between two or more features of the sizing device 105, or qualitatively judging the overall shape of the sizing device 105.

In operational block 240, a comparison is made between the test geometry 132 and a reference pattern 156. The comparison may include measuring or qualitatively noting differences between the reference geometry 130 and the test geometry 132. For example, the values of $L_{Ref}$ and $L_{Test}$ may be compared and the difference noted or saved for later calculations or computations. In certain embodiments, a test image of the sizing device 105 in the eye 12 is compared to a reference image of the sizing device 105 recorded prior to placing the sizing device 105 in the eye 12. The test image and the reference image may be compared using image processing algorithms known in the art in determining changes in geometry of the sizing device 105. Alternatively, the comparison may comprise comparing information in the test geometry 130 with empirical information provided by, for example, a manufacturer or supplier. This empirical information may comprise geometric information of the sizing device 105 in a reference or unstressed state. Alternatively, the information may include correlation data between certain geometric conditions of the sizing device 105 and the overall size of the sizing device 105 or an IOL to be placed inside the eye 12.

In operational block 250, the above comparison is used to determine a size or dimension of the anterior chamber 18. In certain embodiments, the operational block 250 includes correlating a dimension of the test geometry 132 (or change between the reference geometry 130 and the test geometry 132) to a dimension of the anterior chamber 18. In the illustrated embodiment in FIG. 7, this may be accomplished by comparing the reference distance $L_{ref}$ to the test distance $L_{Test}$. For example, a correlation may be established of the distance between the first and second features 168, 170 (e.g., $L_{Ref}$ and $L_{Test}$) to the diameter of the sizing device 105 (e.g., $D_{in}$). This correlation leads, therefore, to a determination of the diameter of the anterior chamber 18 based on the comparison of $L_{Ref}$ to $L_{Test}$.

In this example, the diameter of the anterior, chamber 18 is determined by calculating the diameter $D_{in}$ of the sizing device 105 based on (1) the diameter $D_{out}$ of the sizing device 105 prior to placement in an eye, (2) the reference distance $L_{ref}$ prior to placement in an eye, and (3) the test distance $L_{test}$ subsequent to placement in an eye. Based upon these quantities and the structure and geometry of the first and second legs 115, 116 and the base 125 in the sizing device 105, one of skill in the art is able to use the sizing device 105 to calculate the diameter $D_{in}$, which in turn is correlated to a dimension of the anterior chamber 18 (e.g., a diameter, area, or perimeter around the anterior chamber 18).

In certain embodiments, determination of the diameter $D_{out}$ or of both the diameter $D_{in}$ and the diameter $D_{out}$ may be used to determine the amount of force being exerted on the anterior chamber or the iridocorneal angle 24 by the sizing device 105 and/or an IOL to be subsequently placed inside the eye. For example, the change in diameter of the sizing device 105 from the unstressed state (e.g., $D_{out}$-$D_{in}$) may be correlated to the amount of force produced by the arms 115a-d of the sizing device 105 or by the fixation members of an IOL to be subsequently placed in the eye.

In other embodiments, operational block 250 may include comparing a reference angle (e.g., the angle of one or more of the legs 115, 116 prior to placement of the sizing device 105 within the eye 12) to a test angle (e.g., the angle of one or more of the legs 115, 116 after placement of placement of the sizing device 105 within the eye 12). In yet other embodiments, operational block 250 may include measuring an area of the sizing device or a combination of one or more distances, angle, areas, and/or other measurable aspects of the sizing device 105. In still other embodiments, operational block 250 includes determining only a test distant, a test angle, and/or some other measurable aspect of the test geometry 132, independent of the reference geometry 130. This may be accomplished, for example, by establishing a relationship between the separation of the first and second features 168, 170 to a diameter of the sizing device 105.

The first and second features 168, 170 of the sizing device 105 illustrated in FIG. 7 correspond to the edge portion of the legs 115a and 115b, respectively. It will be appreciated that the structure of the sizing device 105 and the selection of the first and second features 168, 170 in FIG. 7 (or the first and second features 71, 72 in FIG. 3) are exemplary only and that different features and structures may be used in these and other embodiments to better facilitate the sizing of the sizing device 105 within the anterior chamber 18. For instance the first and second features 168, 170 may correspond to the contact portions 120a, 120b. Referring to the IOL 10 illustrated in FIG. 3, in other embodiments, the first feature may be the edge 71 of the leg 42b and the second feature may be the geometric center of the optic 34. The center of the optic 34 may be accurately established, for instance, from a digital image of the IOL 10 using image processing algorithms known in the art. In other embodiments, the sizing device 105 may be used in operational block 250 by comparing (1) a reference angle between two or more features of the sizing device 105 prior to placement in the eye 12 and (2) a test angle between those same features subsequent to placement of the sizing device 105 inside the eye 12. Other methods and relationships of utilizing the reference geometry 130 and/or the test geometry 132 of the sizing device 105 are also consistent with embodiments of the present invention.

In certain embodiments, the geometry of the sizing device 105 and the structure and location of features thereof may be selected to facilitate the ease, sensitivity, and/or accuracy of sizing device 105 in determining the size of the anterior chamber 18. Referring again to FIG. 7, for example, it will be appreciated that the structure of the legs 115a, 115b and the location of the first and second features 168, 170 provide a condition in which small changes in diameter of the circle intersecting the contact portions 120a, 120b result in relatively large changes in the distance between the first and second features 168, 170. In other words, the difference between $L_{ref}$ and $L_{test}$ is greater than the difference between diameter $D_{out}$ of the circle 140 and the diameter $D_{in}$ of the circle 141 (i.e., $[L_{ref}-L_{test}]$ is greater than $[D_{out}-D_{in}]$). Referring to FIG. 3, a similar relationship is noted for the geometry of the IOL 10.

Referring again to FIG. 10, the method 200 may also be used when the measurement device comprises the chart 162 and the reference pattern 156 comprises the plurality of visual representations 138 of the sizing device 105. In such embodiments, the operational block 230 of determining the test geometry 132 preferably comprises noting the relative locations and/or orientations between two or more features of the sizing device 105 or qualitatively judging the overall shape of the sizing device 105. For example, the angle of the legs 115a-d relative to the sides of the body 125 may be observed to form an angle that is obtuse, orthogonal, or acute. If the angle is either obtuse or acute, the amount of variation from an orthogonal condition may be qualitatively determined to be small, intermediate, or large. Alternatively or additionally, the overall shape of the sizing device 105 in the eye 12 may be used to determine a test geometry 132.

When using the chart 162, the operational block 240 of making a comparison between the test geometry 132 and the reference pattern 156 may include comparing the test geometry 132, as determined in the previous paragraph, with the plurality of visual representations 138. From this comparison, it may be determined which of the plurality of visual representations 138 most closely match the test geometry 132. The advantage of this approach is that the practitioner may quickly and easily determine the approximate size of the sizing device 105 with reasonable accuracy.

When using the chart 162, the operational block 250 of determining a dimension of the anterior chamber 18 may comprise reading the text block 164 associated with the visual representation 138 that most closely matches the test geometry 132 of the sizing device 105. The information in the text block 164 may include the size or diameter of an IOL for providing a predetermined fit of the IOL within the anterior chamber 18. Alternatively or additionally, information in the text block 164 may include other data allowing a practitioner to select an IOL providing such a predetermined fit.

Figure 12:
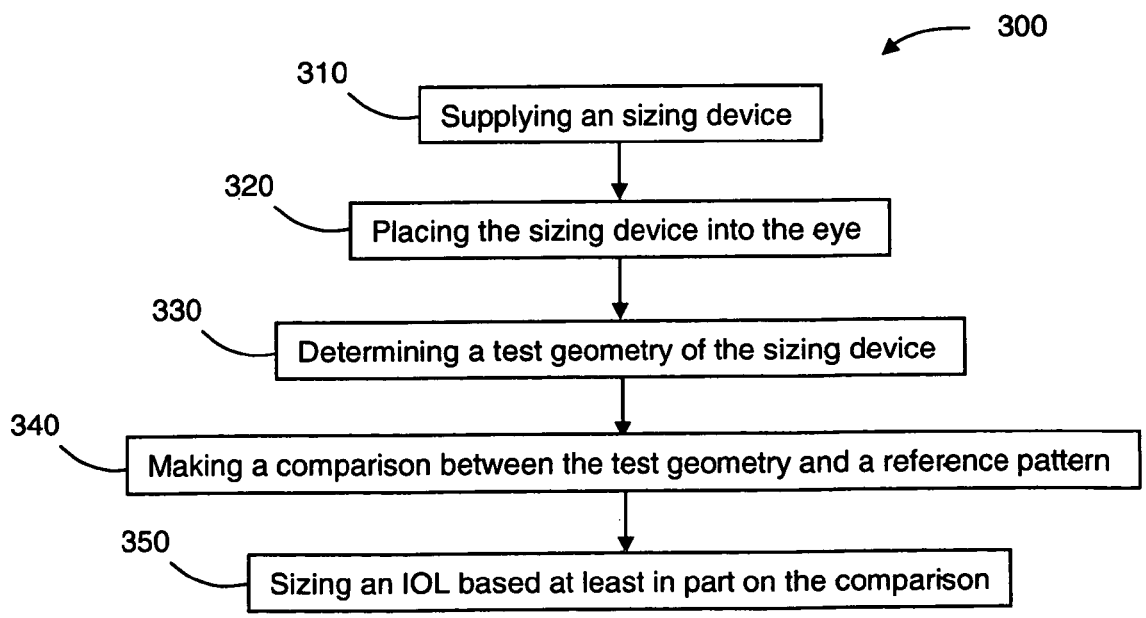
FIG. 12 is a block diagram of a method of sizing an intraocular lens for placement within a region of an eye.

Referring to FIGS. 7-8 and 12, in certain embodiments, a method 300 for sizing an IOL for placement within a portion of an eye, such as the anterior chamber 18 of the eye 12, comprises an operational block 310, which comprises supplying the sizing device 105. The method 300 further comprises an operational block 320, which comprises placing the sizing device 105 into the anterior chamber 18 such that the first and second contact portions 120a, 120b operably engage the iridocorneal angle 24. The method 300 further comprises an operational block 330, which comprises determining the test geometry 132 of the sizing device 105. The method 300 also comprises an operational block 340, which comprises making a comparison between the test geometry 132 and a reference pattern 156. The method 300 additionally comprises an operational block 350, which comprises determining a sizing the IOL based at least in part on the comparison. As with the method 200, the method 300 may be practiced in conjunction with any of the devices or means discussed above herein that are appropriate. In addition, the method 300 may be used for sizing an IOL or other ocular device for placement within other regions of the eye, for example in the capsular bag or sulcus of an eye. For example, the measurement device 110 may be used in practicing the method 300, wherein the measurement device 110 comprises the chart 162 or comprises the camera 158 with the processor 160 and/or the comparison means discussed above herein.

In operational block 350, the sizing device 105 may be configured primarily or exclusively for the purpose of sizing or determining a dimension of the sizing device 105, as illustrated in FIGS. 7 and 8. In such cases, the method 300 may further comprise removing the sizing device 105 from the anterior chamber 18 and replacing it with an IOL that is selected to provide a predetermined fit inside the anterior chamber 18.

In some embodiments, the sizing device 105 is also an IOL such as the IOL 10 illustrated in FIG. 3. In such embodiments, the method 300 may comprise determining at least one dimension of the sizing device/IOL in order to confirm that it is properly sized. Alternatively, the method 300 may comprise determining or estimating the amount of force being produced by the IOL on the eye. The method 300 may also comprise allowing the sizing device 105 may remain in the eye 12 if it is determined that the sizing device 105 provides a predetermined fit in or compressive force on the portion of the eye 12 into which the sizing device 105 has been placed. Alternatively, the method 300 may comprise replacing the sizing device 105 with another IOL or another sizing device that provides a better fit in the eye 12, provides a more appropriate compressive force on the eye 12, or provides some other desired function.

In other embodiments, the sizing device 105 may be reconfigured to form an IOL, for instance when the sizing device 105 comprises the frame 144 and the attachable optic 146, as illustrated in FIG. 9. In such embodiments, the method 300 may comprise determining at least one dimension of the sizing device/IOL or determining the amount of force being produced by the IOL on the eye. In such embodiments, the method 300 may additionally comprise attaching the attachable optic 146 to the frame 144, preferably while the frame 144 is still in the eye 12.

Figure 13:
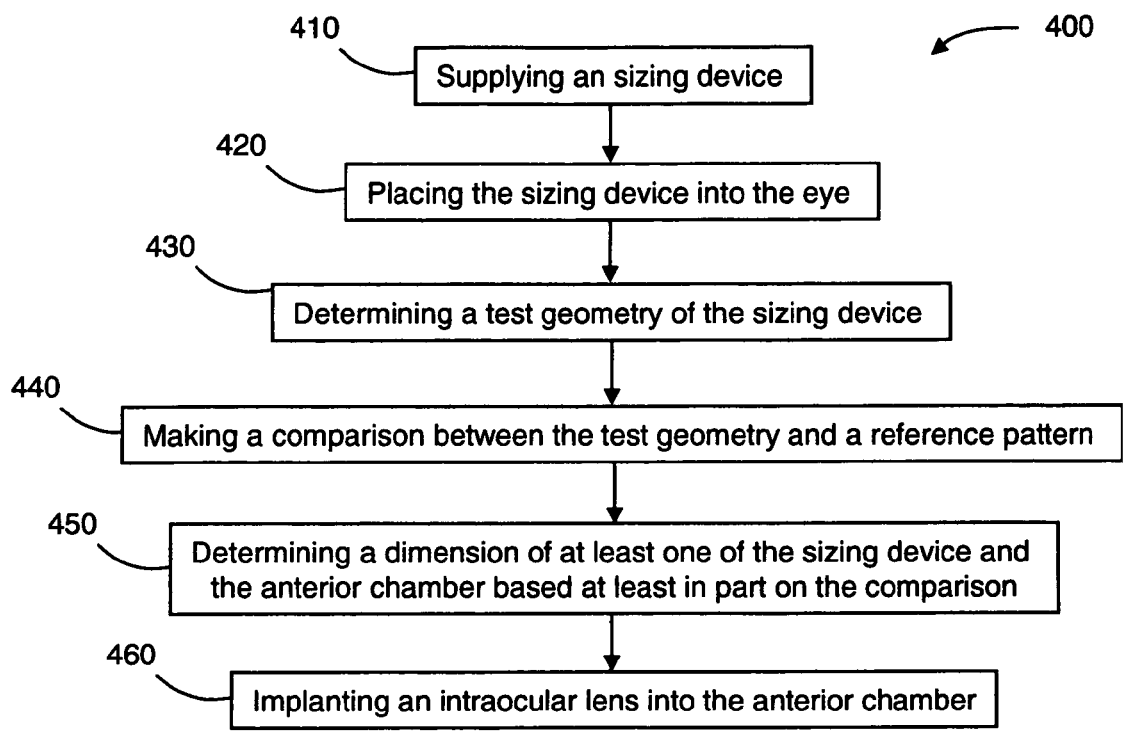
FIG. 13 is a block diagram of a method of implanting an intraocular lens into a region of an eye.

Referring to FIGS. 7-8 and 13, in certain embodiments, a method 400 for implanting an intraocular lens into the anterior chamber 18 of an eye comprises an operational block 410, which comprises supplying the sizing device 105. The method 400 further comprises an operational block 420, which comprises placing the sizing device 105 into the anterior chamber 18 such that the first and second contact portions 120a, 120b operably engage the iridocorneal angle 24. The method 400 further comprises an operational block 330, which comprises determining the test geometry 132 of the sizing device 105. The method 400 also comprises an operational block 440, which comprises making a comparison between the test geometry 132 and a reference pattern 156. The method 400 additionally comprises an operational block 450, which comprises determining a dimension of at least one of the sizing device 105 and the anterior chamber 18 based at least in part on the comparison. The method 400 also comprises an operational block 460, which comprises placing or implanting an IOL into the anterior chamber 18. In certain embodiments, the method 400 additionally comprises reconfiguring the sizing device is reconfigured to form an intraocular lens. As with the methods 200 and 300, the method 400 may be practiced in conjunction with any of the devices or means discussed above herein that are appropriate. In addition, the method 400 may be used for placing or implanting an IOL or other ocular device within other regions of the eye, for example in the capsular bag or sulcus of an eye. For example, the measurement device 110 may be used in practicing the method 400, wherein the measurement device 110 comprises the chart 162 or comprises the camera 158 with the processor 160 discussed above herein.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. An apparatus for sizing at least one of an intraocular lens and a region of an eye, comprising:
a sizing device for placement within an eye, comprising:
a first leg having a first contact portion for operably engaging a first portion of the eye;
a second leg having a second contact portion for operably engaging a second portion of the eye; and
a measurement device for making a comparison between a geometry of the sizing device and the measurement device;
wherein the measurement device is a chart comprising a plurality of visual representations of the sizing device.

2. An apparatus for sizing at least one of an intraocular lens and a region of an eye, comprising:
a sizing device for placement within an eye, comprising:
a first leg having a first contact portion for operably engaging a first portion of the eye;
a second leg having a second contact portion for operably engaging a second portion of the eye; and
a measurement device for making a comparison between a geometry of the sizing device and the measurement device;
wherein the measurement device comprises a reference pattern that is a visual representation of the sizing device.

3. An apparatus for sizing at least one of an intraocular lens and a region of an eye, comprising:
a sizing device for placement within an eye, comprising:
a first leg having a first contact portion for operably engaging a first portion of the eye;
a second leg having a second contact portion for operably engaging a second portion of the eye; and
a measurement device for making a comparison between a geometry of the sizing device and the measurement device;
wherein the measurement device comprises a reference pattern that is empirical information regarding dimensions of the sizing device.

4. An apparatus for sizing at least one of an intraocular lens and a region of an eye, comprising:
a sizing device for placement within an eye, comprising:
a first leg having a first contact portion for operably engaging a first portion of the eye;
a second leg having a second contact portion for operably engaging a second portion of the eye; and
a measurement device for making a comparison between a geometry of the sizing device and the measurement device;
wherein the measurement device comprises a reference pattern that is empirical information correlating a geometric condition of the sizing device and a size of the sizing device.

5. An apparatus for sizing at least one of an intraocular lens and a region of an eye, comprising:
a sizing device for placement within an eye, comprising:
a first leg having a first contact portion for operably engaging a first portion of the eye;
a second leg having a second contact portion for operably engaging a second portion of the eye; and
a measurement device for making a comparison between a geometry of the sizing device and the measurement device;
wherein the measurement device comprises a reference pattern configured for making a comparison between a test geometry of the measurement device and the reference pattern.

6. An apparatus for sizing at least one of an intraocular lens and a region of an eye, comprising:
- a sizing device for placement within an eye, comprising:
    - a first leg having a first contact portion for operably engaging a first portion of the eye;
    - a second leg having a second contact portion for operably engaging a second portion of the eye; and
- a measurement device for making a comparison between a geometry of the sizing device and the measurement device;
- wherein the measurement device illustrates varying amounts of bending of the legs corresponding to varying amounts of compression of the sizing device.

7. An apparatus for sizing at least one of an intraocular lens and a region of an eye, comprising:
- a sizing device for placement within an eye, comprising:
    - a first leg having a first contact portion for operably engaging a first portion of the eye;
    - a second leg having a second contact portion for operably engaging a second portion of the eye; and
- a measurement device for making a comparison between a geometry of the sizing device and the measurement device;
- wherein the sizing device further comprises a test geometry when the sizing device is disposed within a region within the eye.

* * * * *